United States Patent [19]

Matsuda et al.

[11] Patent Number: 5,240,747
[45] Date of Patent: Aug. 31, 1993

[54] PROCESS FOR MODIFYING SURFACES OF MATERIALS

[75] Inventors: Takehisa Matsuda, Minoo; Takashi Sugawara, Ikeda; Kazuhiko Inoue, Kobe; Nobutaka Tani, Osaka, all of Japan

[73] Assignee: Kanegafuchi Kagaku Kogyo Kabushiki Kaisha, Osaka, Japan

[21] Appl. No.: 739,353

[22] Filed: Aug. 2, 1991

Related U.S. Application Data

[63] Continuation-in-part of Ser. No. 520,902, May 9, 1990, Pat. No. 5,128,170.

[30] Foreign Application Priority Data

| May 11, 1989 | [JP] | Japan | 1-118222 |
| Jun. 1, 1989 | [JP] | Japan | 1-140576 |
| Sep. 25, 1989 | [JP] | Japan | 1-248440 |
| Aug. 2, 1990 | [JP] | Japan | 2-206573 |

[51] Int. Cl.$^5$ .................. B05D 3/06; A01N 1/02; C12N 11/06; C12N 11/08
[52] U.S. Cl. .................. 427/512; 427/2; 427/510; 427/520; 435/180; 435/181
[58] Field of Search .................. 427/53.1, 54.1, 55, 427/56.1, 35, 36, 44, 2, 512, 520, 508, 510; 435/177, 180, 181

[56] References Cited

U.S. PATENT DOCUMENTS

| 3,959,078 | 5/1976 | Guire | 435/181 |
| 4,007,089 | 2/1977 | Smith | 435/181 |
| 4,101,380 | 7/1978 | Rubinstein et al. | 435/181 |
| 4,160,698 | 7/1979 | Miyairi et al. | 435/180 |
| 4,206,259 | 6/1980 | Rohrbach et al. | 435/180 |
| 4,273,873 | 6/1981 | Sugitachi et al. | 435/181 |
| 4,539,061 | 9/1985 | Sagiv | 427/506 |
| 4,722,906 | 2/1988 | Guire | 435/177 |
| 4,973,493 | 11/1990 | Guire | 427/2 |
| 5,128,170 | 7/1992 | Matsuda et al. | 427/520 |

FOREIGN PATENT DOCUMENTS

| 0397130 | 11/1990 | European Pat. Off. |
| 1447975 | 1/1969 | Fed. Rep. of Germany |
| 2419802 | 11/1974 | Fed. Rep. of Germany |
| 8802623 | 4/1988 | World Int. Prop. O. |

OTHER PUBLICATIONS

Balachander et al, "Functionalized Siloxy-anchored Monolayers with Exposed amino, Azido, Bromo, or Cyano groups", Tetrahedron Letters, 29, 5593 1988 (no month).

World Patents Index Latest, Week 1388, Derwent Publications Ltd., London, GB: AN 88-089243 & JP-A-63 041 541 Agency of Ind. Sci. Tech. no date.

World Patents Index, Week 3678, Derwent Publications Ltd., London, GB; AN 78-64293A & JP-A—53 088 073 no date.

World Patents Index Latest, Week 487, Derwent Publications Ltd., London, GB; AN 87 025178 & JP-a-61 281 177 Canon-no date.

Patent Abstracts of Japan, vol. 14, No. 343, Jul. 25, 1990 Hidemi et al.

World Patents Index Latest, Week 5088, Derwent Publications Ltd., London, GB; AN 88-356109 & JP-A-63 262 603 Mitsubishi Rayon-no date.

Primary Examiner—Marianne Padgett
Attorney, Agent, or Firm—Armstrong, Westerman, Hattori, McLeland & Naughton

[57] ABSTRACT

A process for modifying the surface of a material such as plastics, metals, glasses and ceramics which comprises the steps of (1) coating a compound having at least one azido group on the surface of the material to be modified, (2) making a modifier substance to be fixed for the modification exist on or in the coated surface, and (3) irradiating ultraviolet rays to the coated surface to fix the modifier substance to the coated surface, wherein various compounds can be used as the modifier for converting the characteristics of the material surface to the desired characteristics without previously treating them, and various materials can be easily modified with a firm fixing of the modifier.

7 Claims, No Drawings

PROCESS FOR MODIFYING SURFACES OF MATERIALS

CROSS-REFERENCE TO RELATED APPLICATION

This is a continuation-in-part of application Ser. No. 07/520,902 filed on May 9, 1990, now U.S. Pat. No. 5,128,170 issued Jul. 7, 1992.

BACKGROUND OF THE INVENTION

The present invention relates to a process for modifying the surfaces of materials.

In recent years, modification or improvement of the surfaces of materials makes an important technology in various fields such as medical care, dyeing and adhesion. Particularly, in the medical field, it is difficult to find a material which simultaneously satisfies the dynamical characteristics and the biocompatibility of the surface thereof and, therefore, it has been attempted to modify the surface of a device made from a material which satisfies required dynamical characteristics, so as to impart a biocompatibility to the device surface.

Representative means for modifying the surface of a material are coating and discharge treatment.

There is proposed a process wherein an azido group is introduced to a compound having characteristics necessary for the modification of the surface of a material, the compound is coated on the material surface to be modified and it is fixed to the material surface through covalent bond by a photochemical reaction of azido group introduced to the compound. The proposed process utilizing a photochemical reaction of azido group has the advantage that the newly formed surface is very stable because the azido group-introduced compound is fixed to the material surface through covalent bond. However, the process has the disadvantages that characteristics desired to modify or improve vary depending on the purposes and the like and, therefore, various azido group-containing modifiers must be prepared by introducing azido group to every compound which has characteristics necessary for the desired modification, and that the process is not applicable to materials with which the nitrene group produced by photochemical reaction of azido group cannot form covalent bond. Also, if a compound which has characteristics desired for the modification of a material surface and to which azido group is introduced, or an aqueous or organic solvent solution thereof is not compatible with the material surface to be modified, it does not contact uniformly or close with the material surface and the azido group-containing compound is not fixed well to the material by photochemical reaction, resulting in unsatisfactory modification.

It is an object of the present invention to provide a process for modifying surfaces of materials, which is applicable with ease to various compounds having characteristics desired for the modification of material surfaces and to various materials to be modified, and which can firmly fix the compounds to the material surfaces.

The above and other objects of the present invention will become apparent from the description hereinafter.

SUMMARY OF THE INVENTION

It has now been found that the surfaces of materials can be simply, easily and stably modified to have the desired characteristics by forming on the material surfaces a layer of a compound having an azido group, e.g. a polymer having an azido group, applying the substance to be fixed on or in the coating layer, for example, by means of coating, impregnation or adsorption, and irradiating with ultraviolet light.

In accordance with the present invention, there is provided a process for modifying the surface of a material which comprises the steps of
(1) coating a compound having at least one azido group onto the surface of the material to be modified,
(2) applying a modifier substance to be fixed for on or in the coated surface,
(3) irradiating ultraviolet rays to the coated surface in the step (2), thereby fixing the modifier substance, and
(4) removing the modifier substance unfixed in the step (3).

In the process of the present invention, a coatable compound having an azido group such as an azido-containing polymer is previously coated on the material surface to be modified, a modifier substance to be fixed for the modification of the material surface is then made to exist on or in the coated surface by a suitable means, e.g. coating, impregnation or adsorption, and the material surface is irradiated with ultraviolet rays, whereby the modifier substance is fixed by means of covalent bond resulting from photochemical reaction of azido group to the material surface through the coating layer. Accordingly, various substances can be used as the modifiers without any treatment. Also, since a suitable azido-containing compound is selected and used in accordance with the material to be modified or the modifier material to be fixed, various materials can be modified and moreover the modifier material can be firmly fixed to the material surface through the azido-containing compound. Further, when ultraviolet rays are irradiated imagewise or patternwise or to only the desired portion of the material surface, it is possible to modify on the desired portion of the material surface.

DETAILED DESCRIPTION

In the present invention, a compound having at least one azido group which is coatable in the form of an aqueous or organic solvent solution or dispersion onto the material surface to form a uniform layer, is firstly coated onto the material surface.

The compound having at least one azido group may be a high molecular weight compound (polymer) or a low molecular weight compound. In particular, the azido group-containing polymer is advantageous for use in the modification of the surface of materials which cannot form a covalent bond with nitrene group produced by photochemical reaction of azido group, because the polymer itself can physically firmly adhere to the material surface.

The modifier substance can be fixed to the material surface through the azido group-containing compound so long as at least one azido group is present per molecule of the compound, but the compound having two or more azido groups is preferred because it can bond at two or more points with the modifier substance to be fixed or with both the modifier substance and the material surface, thus the fixing of the modifier substance can be more stably achieved.

Examples of the azido group-containing polymer are, for instance, a homopolymer of an azido group-containing vinyl monomer such as azidostyrene or a methacrylate to which azido group is introduced, a copolymer of the azido group-containing vinyl monomer with a vinyl monomer containing no azido group such as styrene, styrene sulfonate, methyl methacrylate, acrylamide or dimethylacrylamide, and a polymer to which at least one azido group is introduced after the preparation of the polymer. Copolymers of the azido group-containing vinyl monomer with styrene, methyl methacrylate or dimethylacrylamide are preferred because the coating can be stably carried out. The polymer to which at least one azido group is introduced can be prepared, for instance, by a method wherein an amino group-containing azido compound is condensed with carboxyl group of a carboxyl group-containing polymer in the presence of a condensing agent, a method wherein an azido compound having acid chloride group or aldehyde group is reacted with hydroxyl group of a hydroxyl group-containing polymer, a method wherein a carboxyl group-containing azido compound is condensed with amino group of an amino group-containing polymer in the presence of a condensing agent, a method wherein an azido compound having N-hyroxysuccinimide ester group or epoxy group is reacted with an amino group-containing polymer, or a method wherein an amido group-containing polymer such as polyacrylamide is treated in a known manner, e.g. Hofmann degradation, to convert amido group into amino group, and azido group is introduced utilizing the amino group.

A higher content of the units of the azido group-containing monomer in the copolymer is preferred from the viewpoint of formation of stable bonding with the modifier substance. The content of the azido group-containing monomer units in the copolymer is at least 1% by mole, especially at least 10% by mole.

The molecular weight of the azido group-containing polymer is not particularly limited. From the viewpoint of formation of a stable coating layer, however, it is desirable that the polymer has a number average molecular weight of at least 10,000, especially at least 100,000.

Examples of the low molecular weight compound having at least one azido group are, for instance, a known bisazido compound as used in a photoresist material, and a compound having a functional group, which has an affinity for a special functional group of the material surface, as well as an azido group. The azido group-containing low molecular weight compounds used in the present invention are not limited thereto.

In case of the low molecular weight compound, it is hard to expect that the compound coated on the material surface firmly adheres to the material surface by film formation as achieved in the case of the polymer. Accordingly, it is preferable that the low molecular weight compound has at least two azido groups so that it can combine with both the material surface to be modified and the modifier substance to be fixed. Representative examples of the bisazido compound are shown in Table 1.

TABLE 1

| Bisazido compound | Photo-sensible range |
|---|---|
| $N_3$—⌬—$CH_2$—⌬—$N_3$ | deep UV |

TABLE 1-continued

| Bisazido compound | Photo-sensible range |
|---|---|
| $N_3$—⌬(Cl)—$CH_2$—⌬(Cl)—$N_3$ | " |
| $N_3$—⌬—O—⌬—$N_3$ | " |
| $N_3$—⌬—$SO_2$—⌬—$N_3$ | " |
| $N_3$—⌬—$SO_2$—⌬—$N_3$ (meta) | " |
| $N_3$—⌬—SS—⌬—$N_3$ | " |
| $N_3$—⌬—S—⌬—$N_3$ | " |
| $N_3$—⌬($OCH_3$)—⌬($OCH_3$)—$N_3$ | i-line |
| $N_3$—⌬—CH=CH—⌬—$N_3$ | i-line |
| $N_3$—⌬—CH=CH—C(=O)—⌬—$N_3$ | " |
| $N_3$—⌬—CH=CH—C(=O)—CH=CH—⌬—$N_3$ | " |
| $N_3$—⌬—CH=(cyclohexanone)=CH—⌬—$N_3$ | " |
| $N_3$—⌬—CH=(methylcyclohexanone)=CH—⌬—$N_3$ | " |
| $N_3$—⌬($SO_3Na$)—CH=CH—⌬($NaO_3S$)—$N_3$ | " |
| $N_3$—⌬—CH=CH—CH=(t-Bu cyclohexanone)=CH—CH=CH—⌬—$N_3$ | g-line |

The azido group may be, for instance, carbonylazido group (—$CON_3$), sulfonylazido group (—$SO_2N_3$) and the aromatic azido group

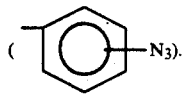

The process of the present invention is applicable to various materials for the modification of the surface thereof. Examples of the material to be modified, namely the material to be coated with the azido group-containing compound, are, for instance, plastics, metals, glass and ceramics. The shape or surface condition of the material are not particularly limited. Since the coating can be easily achieved, for instance, by spraying or immersion, and can be stably supported on the material surface even if the material has a complicated shape or a rough surface, the process of the invention is applicable directly to devices molded or processed, the surface of which is desired to modify.

The low molecular weight and high molecular weight compounds having at least one azido group are coated on the material surface in the form of a solution or dispersion in water or an organic solvent, preferably a volatile organic solvent, in a usual manner such as casting, spraying, immersion or the like, and then dried. The solvent is suitably selected according to the kinds of the material to be coated and the azido group-containing compound.

The thickness of the coating layer is preferably from about 0.1 to about 1 μm for the azido group-containing polymer from the viewpoint that a stable coating film can be formed. In case of the low molecular weight compound having an azido group, it is preferable that a molecular layer of monomolecule to several molecules or a layer having a thickness corresponding to such a molecular layer is formed on the material surface so that a stable coating layer can be formed and accordingly the modifier substance can be stably fixed.

A modifier substance to be fixed for the modification of the material is made to exist in or on the surface coated with the compound having at least one azido group.

The modifier substance usable in the process of the present invention is not particularly restricted so long as it is an organic substance, e.g. synthetic polymers and natural high molecular compounds, and has a site capable of combining with an azido group by light irradiation. It is desirable that the modifier substance is easy to be adsorbed by the surface coated with the azido group-containing compound or is easily retained on the coated surface so that the subsequent light irradiation step can be practiced without difficulty. For instance, as the synthetic polymers used as the modifier substance, there are mentioned non-ionic hydrophilic polymers such as polyacrylamide and polyethylene glycol which are preferable when it is desired to convert the material surface to an anti-thrombogenic surface, and hydrophobic polymers. The natural high molecular compounds used as the modifier substance include, for instance, proteins, enzymes and saccharides.

The modifier substance to be fixed can be made to exist in or on the coated surface in various manners, for instance, by coating an aqueous or organic solvent solution or dispersion in the same manner as in the coating of the azido group-containing compound, or by immersing the material coated with the azido group-containing compound in a colloidal solution, suspension or aqueous solution of the modifier substance thereby making the coating layer of the azido group-containing compound adsorb the modifier substance.

The amount of the modifier substance to be retained in or on the coating layer of the azido group-containing compound is not particularly limited.

The material surface onto which the azido group-containing compound and the modifier substance have been applied, is then irradiated with a light such as ultraviolet rays, whereby the fixing of the modifier substance is completed in a short period of time. As a light source for the irradiation operation, there can be used various kinds of mercury light used generally as a source for ultraviolet rays, such as a high pressure mercury lamp, a low pressure mercury lamp or an extra-high pressure mercury lamp.

When the modifier substance has been adsorbed by the coating layer in the manner mentioned above using aqueous solution, colloidal solution or suspension, the fixing can be achieved also by irradiating ultraviolet rays from above the solution and the like. This procedure is suitable particularly for the fixing of biologically active proteins, enzymes and the like.

The irradiation conditions of ultraviolet rays are not particularly limited. For instance, ultraviolet rays may be irradiated directly from a usual mercury lamp. Since the reaction of nitrene group proceeds promptly, irradiation in 5 minutes is usually enough for the fixing treatment. In case of fixing proteins and enzymes, it is preferable to conduct the irradiation by cutting off the shorter wavelength region below 320 nm using a filter, whereby damage of proteins and enzymes by shorter wavelength ultraviolet rays is prevented.

The irradiation may be conducted imagewise or patternwise or to only a desired portion of the material surface using a photomask or photolithography, whereby the modifier substance can be fixed to only the exposed portion of the material surface.

After the irradiation of ultraviolet rays, the unfixed modifier substance is removed by rinsing the irradiated material with a solvent such as water, metanol or other suitable organic solvents which can dissolve the modifier substance but does not dissolve the material to be modified.

According to the process of the present invention, the formed layer of the modifier substance can be stably retained on the material surface, because when an azido group-containing polymer is used for forming the coating layer of azido group-containing compound, there are formed covalent bonds between the modifier substance and the coated polymer, and crosslinkages intermolecularly and intramolecularly in the coated polymer. Further, when the material to be modified is a plastic material or the like, the modifier layer can be more stably retained on the material surface because covalent bonds are also produced between the material surface and the coated polymer. Also in case of using a low molecular weight compound having an azido group, the modifier substance is stably retained on the material surface in a like manner.

The present invention is more specifically described and explained by means of the following Examples, in which all percentages are by weight unless otherwise noted. It is to be understood that the present invention is not limited to these Examples.

In order to illustrate the preparation of a vinyl monomer containing azido group and a polymer containing azido group, the following Reference Examples are also given.

REFERENCE EXAMPLE 1

Synthesis of azidostyrene

In a mixture of 10 ml of ethanol and 10 ml of conc. hydrochloric acid was suspended 5 g of 3-nitrostyrene. To the suspension was added a solution of 22.3 g of SnCl$_2$. 2H$_2$O in 10 ml of ethanol with vigorously stirring, and the suspension was allowed to stand at room temperature overnight.

After neutralizing the suspension with NaOH, the solid matter was filtered off, and the product was extracted from the filtrate with an ether.

The ether layer was dehydrated with MgSO$_4$, and thereto was added conc. hydrochloric acid to give an intermediate compound of the formula (1):

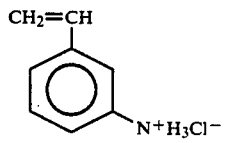

In a mixture of 20 ml of water and 2 ml of conc. sulfuric acid was dissolved 2.4 g of the intermediate compound (1), and a 1N NaNO$_2$ aqueous solution was added to the resulting solution with ice cooling. After 1.5 hours, an aqueous solution of 1.6 g of NaN$_3$ was gradually added to the solution. The solution was then stirred at room temperature for 3 hours. The solution was extracted with ethyl acetate, and the ethyl acetate layer was washed with a 0.1N NaHCO$_3$ aqueous solution and then with water and was dried with MgSO$_4$.

After distilling away, ethyl acetate, the residue was dissolved in a mixed solvent of chloroform and hexane (¼ by volume), and was purified by a silica gel column. The solvent was distilled away to give 3-azidostyrene.

Synthesis of azidostyrene-styrene copolymer

One mole of 3-azidostyrene and 4 moles of styrene were diluted 4 times with benzene, and 0.01 equivalent of N,N'-azobisisobutyronitrile (AIBN) as an initiator was added to the monomer solution. After degassing and sealing the reactor, the polymerization was carried out at 60° C. for 3 hours.

After allowing to cool, the reaction mixture was poured into a large quantity of methanol to precipitate the produced azidostyrene-styrene copolymer. The copolymer had a number average molecular weight of 100,000.

REFERENCE EXAMPLE 2

Synthesis of azidobenzoyloxyethyl methacrylate

In 100 ml of N,N'-dimethylformamide (DMF) was dissolved 10 g of p-azidobenzoic acid, and the resulting solution was cooled with ice. To the solution were added 8.5 ml of triethylamine and then 8.3 ml of isobutyl chloroformate.

A solution of 5.2 ml of hydroxyethyl methacrylate in 300 ml of DMF was then added to the above solution, and the reaction was carried out at 60° C. for 5 hours with stirring.

After distilling away the solvent from the reaction mixture, the residue was extracted with ethyl acetate. The ethyl acetate portion was washed with a 10% aqueous solution of citric acid, water, a 4% aqueous solution of NaHCO$_3$ and water in that order, and was dried with anhydrous NaSO$_4$.

After distilling away ethyl acetate, the residue was dissolved in chloroform and was purified by a silica gel column. The solvent was distilled away to give azidobenzoyloxyethyl methacrylate.

Synthesis of azidobenzoyloxyethyl methacrylate-methyl methacrylate copolymer

One mole of azidobenzoyloxyethyl methacrylate and 4 moles of methyl methacrylate were diluted about 2 times with DMF, and 0.01 equivalent of AIBN initiator was added to the monomer solution. After degassing and sealing the reactor, the polymerization was carried out at 60° C. for 3 hours.

After allowing to cool, the reaction mixture was poured into a large quantity of ethyl ether to precipitate the produced azidobenzoyloxyethyl methacrylate-methyl methacrylate copolymer. The copolymer had a number average molecular weight of 150,000.

EXAMPLE 1

The azidostyrene-styrene copolymer prepared in Reference Example 1 was dissolved in acetone to give a 1% solution.

On a polyethylene terephthalate (PET) film having a surface area of about 2 cm$^2$ was cast 20 μl of the copolymer solution, and it was dried to form a film of azidostyrene-styrene copolymer having a thickness of 1 μm.

The coated PET film was immersed for 1 hour in a 5.0% solution of albumin in a phosphoric acid buffer (pH 7.4) to adsorb albumin. The film was taken out and irradiated with ultraviolet rays for 1 minute using a high pressure mercury lamp.

The film was thoroughly washed with water and dried, and it was confirmed by electron spectroscopy for chemical analysis (ESCA) that albumin was fixed to the coated PET film.

EXAMPLE 2

The fixing of albumin was carried out in the same manner as in Example 2 except that a glass thin plate of about 2 cm$^2$ was used instead of the PET film.

After thoroughly washing the treated glass plate with water and drying, it was confirmed by ESCA that albumin was fixed.

EXAMPLE 3

The fixing of fibronectin was carried out in the same manner as in Example 1 except that a copper thin plate of about 2 cm$^2$ and fibronectin were used instead of the PET film and albumin, respectively.

After thoroughly washing the treated plate with water and drying, the fixing of fibronectin was confirmed by ESCA.

EXAMPLE 4

The azidobenzoyloxyethyl methacrylate-methyl methacrylate copolymer prepared in Reference Example 2 was dissolved in acetone to give a 1.0% solution.

On a PET film having a surface area of about 2 cm$^2$ was cast 20 μl of the copolymer solution, and it was dried to form a coating film of azidobenzoyloxyethyl methacrylate-methyl methacrylate copolymer having a thickness of 1 μm.

On the coating layer was cast 20 μl of a 1.0% methanol solution of poly-N,N-dimethylacrylamide having a molecular weight of about 100,000. After drying, the thus coated PET film was irradiated for 1 minute with ultraviolet rays using a high pressure mercury lamp.

After washing the irradiated PET film with methanol in a Soxhlet extractor and drying, the fixing of poly-N,N-dimethylacrylamide was confirmed by ESCA.

EXAMPLE 5

The fixing of polyethylene glycol was carried out in the same manner as in Example 4 except that a glass thin plate having a surface area of about 2 cm$^2$ and polyethylene glycol having a molecular weight of about 50,000 were used instead of the PET film and poly-N,N-dimethylacrylamide, respectively.

After washing the treated glass plate with methanol in a Soxhlet extractor and drying, the fixing of polyethylene glycol was confirmed by ESCA.

EXAMPLE 6

The azidobenzoyloxyethyl methacrylate-methyl methacrylate copolymer prepared in Reference Example 2 was coated on a stainless steel thin plate having a surface area of about 2 cm$^2$ in the same manner as in Example 4.

Albumin was fixed using the coated stainless steel plate in the same manner as in Example 1.

After thoroughly washing the thus treated plate with water and drying, the fixing of albumin was confirmed by ESCA.

In addition to the ingredients used in the Examples, other ingredients can be used in the Examples as set forth in the specification to obtain substantially the same results.

What we claim is:

1. A process for modifying the surface of a material with a modifier substance which consists essentially of:

coating the surface of the material to be modified with a solution or dispersion containing a polymer containing at least one azido group and having a number average molecular weight of at least 10,000.

applying the modifier substance to the surface coated with said polymer, irradiating the modifier substance with ultraviolet light to react the modifier substance with an azido group of the polymer and to fix the modifier substance to the polymer, and washing the surface of the material coated with polymer to remove unreacted modifier substance.

2. The process of claim 1, wherein the polymer is a homopolymer or copolymer of a vinyl monomer containing an azido group.

3. The process of claim 2, wherein the copolymer is a copolymer comprising at least 1% by mole of the vinyl monomer containing the azido group.

4. The process of claim 1, wherein the modifier substance is applied by coating a solution or dispersion of the modifier substance onto the surface coated with the polymer.

5. The process of claim 1, wherein the modifier substance is applied by immersing the coated material in an aqueous solution, colloidal solution or suspension of the modifier substance, and irradiating the coated material in the aqueous solution, colloidal solution or suspension with ultraviolet light.

6. The process of claim 1, wherein the modifier substance is a hydrophilic polymer, a hydrophobic polymer, a protein, an enzyme or a saccharide.

7. The process of claim 1, wherein only a selected portion of the surface coated with the polymer to which the modifier substance been applied is irradiated.

* * * * *